United States Patent [19]  [11] 4,356,339
Imaizumi et al.  [45] Oct. 26, 1982

[54] PROCESS FOR ISOLATING AND RECOVERING BUTENE-1 OF HIGH PURITY

[75] Inventors: Masao Imaizumi, Tokyo; Tetsuya Takezono, Kawasaki; Takaaki Amari, Yokohama; Yutaka Oguchi, Tokyo, all of Japan

[73] Assignee: Nippon Oil Company, Limited, Tokyo, Japan

[21] Appl. No.: 328,317

[22] Filed: Dec. 7, 1981

[30] Foreign Application Priority Data

Dec. 15, 1980 [JP] Japan ............... 55-176882
Dec. 15, 1980 [JP] Japan ............... 55-176883
Dec. 15, 1980 [JP] Japan ............... 55-177008
Jul. 11, 1981 [JP] Japan ............... 56-108685

[51] Int. Cl.$^3$ .............................. C07C 7/12
[52] U.S. Cl. .................... 585/829; 585/515; 585/517; 585/809; 585/811; 585/830; 526/65; 526/68
[58] Field of Search ............... 585/809, 829, 830, 515, 585/517, 525; 422/234, 235; 526/60, 61, 64, 65, 67, 68; 203/DIG. 6

[56] References Cited

U.S. PATENT DOCUMENTS 4,215,011 7/1980 Smith, Jr. .......... 203/DIG. 6
4,313,016 1/1982 Manning .............. 585/515
4,328,186 5/1982 Karam ............. 422/235 X

FOREIGN PATENT DOCUMENTS 250290 3/1964 Australia ............ 585/515
1197076 7/1965 Fed. Rep. of Germany ...... 585/671

Primary Examiner—Delbert E. Gantz
Assistant Examiner—A. Pal
Attorney, Agent, or Firm—Jordan and Hamburg

[57] ABSTRACT

A process for isolating and recovering butene-1 of high purity at a high yield is provided. The process comprises the steps of continuously passing a butane-butene fraction containing 0.1 to 15 wt % of isobutylene and 10 to 50 wt % of butene-1 through a first reactor packed with a strongly acidic cation exchange resin having an average particle size of from 0.2 to 10 mm at a temperature of from 30° to 100° C. and at a space velocity of liquid of from 0.1 to 50 hr$^{-1}$ under a pressure of from 1 to 50 atm., dividing the output mixture flowing out of said first reactor into two flows at a division ratio in flow rate of 1~15:1, recirculating the first flow having the flow rate of 1~15 into said first reactor packed with said cation exchange resin, passing the second flow having the flow rate of 1 through a second reactor packed with a strongly acidic cation exchange resin under the conditions similar to those of the first reactor, distilling the output flow from said second reactor to separate the same into a heavy hydrocarbon fraction containing oligomers of isobutylene and a light hydrocarbon fraction containing butane and butene, and rectifying said light hydrocarbon fraction to isolate butene-1 from other C$_4$-hydrocarbons.

11 Claims, 1 Drawing Figure

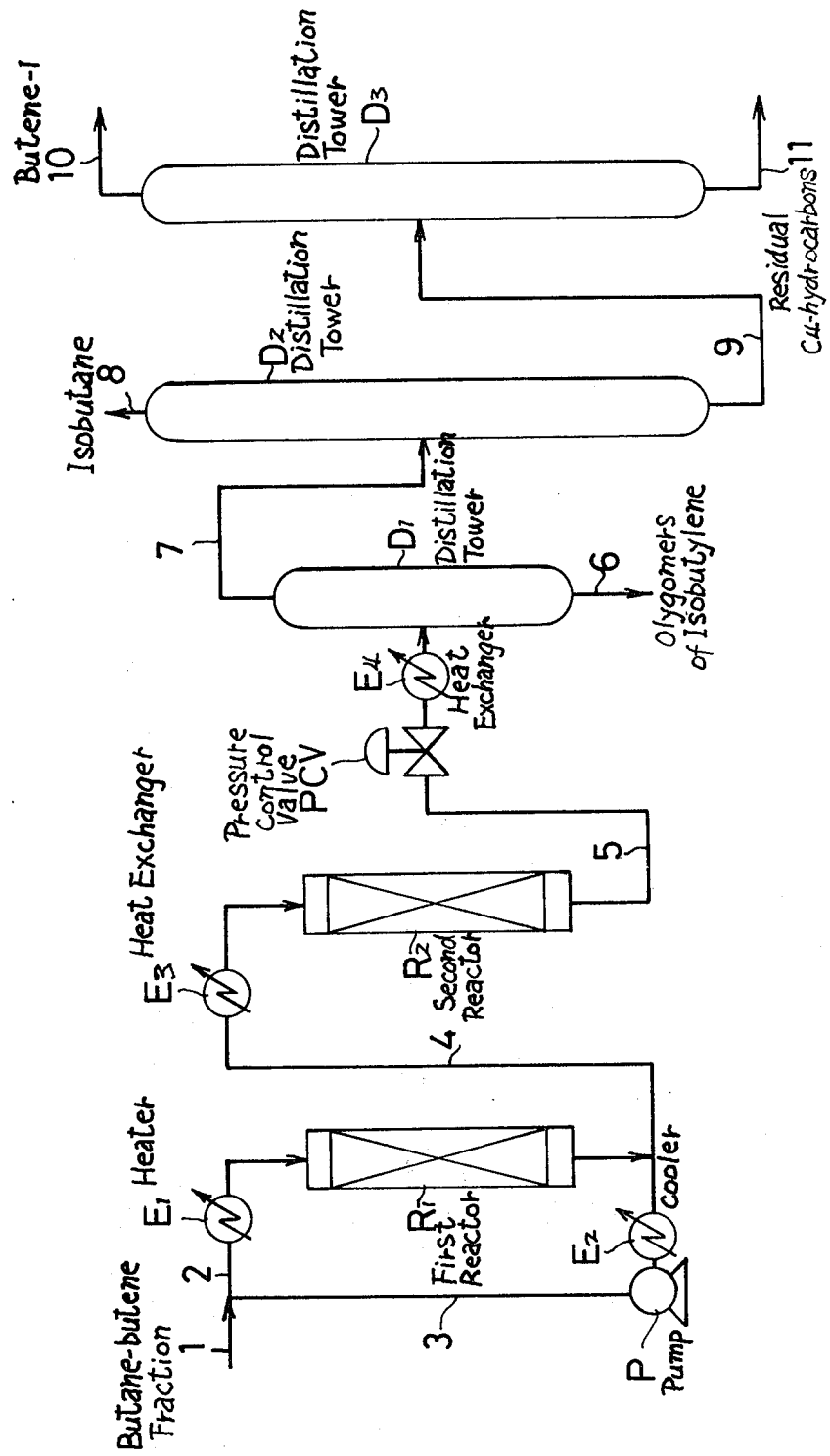

PROCESS FOR ISOLATING AND RECOVERING BUTENE-1 OF HIGH PURITY

BACKGROUND OF THE INVENTION

1. Field of the Invention

This invention relates to a process for isolating and recoverying butene-1 of high purity at a high yield from a butane-butene fraction containing isobutylene and butene-1.

2. Prior Art

In order to isolate butene-1 from a butane-butene fraction containing isobutylene and butene-1, C$_4$-hydrocarbons other than butene-1 must be removed from the fraction by rectification. However, isobutylene cannot be removed by a simple distillation operation since the volatility of isobutylene resembles closely to that of butene-1, in other words the difference in relative volatility between them is too small. For this reason, butene-1 of high purity could not be isolated through a simple distillation or rectification process.

In order to isolate butene-1 of high purity from a butane-butene fraction containing isobutylene and butene-1, it is essential to remove isobutylene from the fraction substantially completely.

One of the known processes for removing isobutylene from the butane-butene fraction is the extraction process by the use of sulfuric acid. However, this known process requires a vast investment because an expensive material must be used for the facilities or apparatuses for effecting the process so that they withstand the corrosive action of sulfuric acid. Another known method of separating isobutylene is the absorption method by the use of zeolite. However, butene-1 cannot be satisfactorily separated from butene-2 by this known method.

In general, isobutylene is dimerized or polymerized by the use of an acidic catalyst. It has been proposed to remove the thus formed dimer and/or polymers from the butane-butene fraction by distillation. However, during this dimerization or polymerization reaction, butene-1 tends to be isomerized to be converted to butene-2. There is also a tendency that butene-1 is copolymerized with isobutylene to form co-oligomers.

It is, therefore, necessary to polymerize isobutyelene while suppressing the undesired side reactions as little as possible in order to isolate and recover butene-1 at a high yield.

OBJECTS AND SUMMARY OF THE INVENTION

A primary object of this invention is to provide a process for isolating and recovering butene-1 of high purity at a high yield.

Another object of this invention is to provide a process for isolating and recovering butene-1 of high purity from a butane-butene fraction containing isobutylene and butene-1, by which process isobutylene is removed substantially completely.

A further object of this invention is to provide a process for isolating and recovering butene-1 of high purity from a butane-butene fraction containing isobutylene and butene-1, wherein isobutylene is polymerized or oligomerized and the formed oligomers of isobutylene are removed without causing any undesired side reactions, such as isomerization of butene-1 or copolymerization of butene-1 and isobutylene.

The above and other objects of this invention will become apparent referring to the following description.

According to this invention, there is provided a process for isolating and recovering butene-1 of high purity at a high yield comprising the steps of continuously passing a butane-butene fraction containing 0.1 to 15 wt% of isobutylene and 10 to 50 wt% of butene-1 through a first reactor packed with a strongly acidic cation exchange resin having an average particle size of from 0.2 to 10 mm at a temperature of from 30° to 100° C. and at a space velocity of liquid of from 0.1 to 50 hr$^{-1}$ under a pressure of from 1 to 50 atm., dividing the output mixture flowing out of said first reactor into two flows at a division ratio in flow rate of 1~15:1, recirculating the first flow having the flow rate of 1~15 into said first reactor packed with said cation exchange resin, passing the second flow having the flow rate of 1 through a second reactor packed with a strongly acidic cation exchange resin having an average particle size of from 0.2 to 10 mm at a temperature of from 30° to 100° C. and at a space velocity of liquid of from 0.1 to 50 hr$^{-1}$ under a pressure of from 1 to 50 atm., distilling the output flow from said second reactor to separate the same into a heavy hydrocarbon fraction containing oligomers of isobutylene as the main ingredient and a light hydrocarbon fraction containing butane and butene as the main ingredients, and rectifying said light hydrocarbon fraction to isolate butene-1 from other C$_4$-hydrocarbons.

BRIEF DESCRIPTION OF THE DRAWING

The single FIGURE appended to the specification is a flow diagram showing an embodiment of the process of this invention.

DESCRIPTION OF THE INVENTION

The present invention will now be described in detail hereinafter.

The starting material used in this invention is a butane-butene fraction containing 0.1 to 15 wt% of isobutylene and 10 to 50 wt% of butene-1. Such a material may be available from C$_4$-fractions prepared by the thermal cracking, steam cracking or catalytic cracking of petroleum. The starting material generally used in this invention is deprived of butadiene substantially completely, for instance to a content of less than 0.1 wt%.

In general, such a starting material contains butene-2, isobutane and n-butane, in addition to isobutylene and butene-1. A starting material containing more than 15 wt% of isobutylene cannot be effectively used. It is preferred that the content of isobutylene be 1 to 10 wt% and the content of butene-1 be 20 to 40 wt%.

It is particularly preferred that the starting material used in the present invention be saturated with water. In the course of developing this invention, we have found that the yield of butene-1 is further increased and the lifetime of the used catalyst is considerably prolonged when the butane-butene fraction containing isobutylene and butene-1 is saturated with water.

One example of the preferable starting material, i.e. starting butane-butene fraction used in this invention is a mixture of unreacted C$_4$-hydrocarbons obtained at the step of the preparation of a liquid or semi-solid polymer by polymerizing a mixture of starting C$_4$-hydrocarbons in the presence of an aluminum chloride catalyst, said starting C$_4$-hydrocarbons being those which are obtained by cracking petroleum and from which butadiene is separated and removed. If it is desired to use the mixture of $C_4$-hydrocarbons saturated with water, such $C_4$-hydrocarbon mixture saturated with water may be prepared by washing the mixture of unreacted $C_4$-hydrocarbons with water.

It has hitherto been known to prepare a liquid or semi-solid polymer (polybutene) by polymerizing isobutylene contained in the mixture of $C_4$-hydrocarbons by subjecting the starting mixture of $C_4$-hydrocarbons deprived of butadiene to polymerization step in the presence of an aluminum chloride catalyst. Although the mixture of unreacted $C_4$-hydrocarbons after the polymerization reaction is reduced in content of isobutylene, it still contains about 1 to 10 wt%, generally 2 to 6 wt% of isobutylene. Butene-1 of high purity could not be obtained even if the mixture of unreacted $C_4$-hydrocarbons was directly subjected to distillation, and it was a common practice to consume the mixture as a fuel. In the process of this invention, such a mixture of unreacted $C_4$-hydrocarbons may be used as a preferable starting material.

Another example of the preferable starting butane-butene fraction used in this invention is a mixture of unreacted $C_4$-hydrocarbons obtained at the step of the preparation of methyl tert-butyl ether by reacting a mixture of starting $C_4$-hydrocarbons with methanol in the presence of an acidic catalyst, said starting $C_4$-hydrocarbons being those which are obtained by cracking petroleum and from which butadiene is separated and removed. It has hitherto been knwon in the art to prepare methyl tert-butyl ether by reacting methanol with isobutylene contained in a mixture of $C_4$-hydrocarbons deprived of butadiene in the presence of a strongly acidic cation exchange resin which is the same as used in this invention. The mixture of unreacted $C_4$-hydrocarbons after being processed through this known method still contains 1 to 10 wt% of isobutylene and has been generally consumed as a fuel. However, according to this invention, such a mixture of unreacted $C_4$-hydrocarbons can be advantageously used as a valuable starting material. If it is desired to saturate the aforementioned mixture of unreacted $C_4$-hydrocarbons with water, the mixture may be washed with water.

A further example of the preferable starting butane-butene fraction used in this invention is a mixture of unreacted $C_4$-hydrocarbons obtained at the step of the preparation of tert-butyl alcohol by reacting a mixture of starting $C_4$-hydrocarbons with water in the presence of an acidic catalyst, said starting $C_4$-hydrocarbons being those which are obtained by cracking petroleum and from which butadiene is separated and removed. It has hitherto been known to prepare tert-butyl alcohol from the $C_4$-hydrocarbon fraction deprived of butadiene by reacting the fraction with water in the presence of an acidic catalyst, such as sulfuric acid, hydrochloric acid or a cation exchange resin which is the same as used in the present invention, to hydrate isobutylene contained in the $C_4$-hydrocarbon fraction. The mixture of unreacted materials obtained by this known process contains generally 1 to 10 wt% of isobutylene, and has commonly been consumed as a fuel. According to this invention, the aforementioned mixture of unreacted $C_4$-hydrocarbons may be advantageously used as a valuable starting material. Meantime, since an excess amount of water over the stoichiometric ratio to isobutylene is normally used at the step of the preparation of tert-butyl alcohol, water forms azeotropic mixtures with unreacted $C_4$-hydrocarbons at the subsequent distillation step of isolating tert-butyl alcohol to be entrained in the resultant mixture of unreacted $C_4$-hydrocarbons. Therefore, even if it is desired to saturate the mixture with water, it is not essential to subject the mixture to washing operation. However, the mixture may be washed with water, as desired.

The butane-butene fraction containing 0.1 to 15 wt% of isobutylene and 10 to 50 wt% of butene-1 as used in this invention may be saturated with water by washing with water in accordance with an ordinary washing operation. In detail, the butane-butene fraction may be allowed to contact with water through a batch process, or may be processed by a continuous counter-current system to allow the butane-butene fraction to contact with water. The butane-butene fraction from which condensed water is separated using a coalescer, is saturated with water and may be used as the starting material in the process of this invention.

In the process of this invention, the aforementioned starting butane-butene fraction is subjected to two-stage reactions by passing the same through two reactors packed with, respectively, any of the strongly acidic cation exchange resins as will be described hereinafter.

More specifically, in the present invention, the reaction tower is divided into two sections or reactors, and the starting material is fed initially to a first reactor. The reaction mixture passing through the first reactor is divided into two flows, the first flow being fed to a succeeding second reactor and the other flow being recirculated into the first reactor. The ratio, in weight, of these two flows in the aforementioned recyclic operation is such that the weight of the second flow, i.e. the recycled or recirculated flow, is 1 to 15 times, preferably 3 to 7 times, as high as that of the first flow. Generally, the second flow is passed through the second reactor only by one time.

In the process of this invention, the reaction tower is divided into two sections or reactors, and the material is fed to the first reactor in the recycle fashion and the material is passed through the second reactor only by one time for the following reason. Since the reaction for producing oligomers of isobutylene utilized in this invention is an exothermic reaction, the difference in temperature between the inlet port and the outlet port of the first reactor is increased to raise the temperature at the vicinity of the outlet port if the first reactor is not operated in the recycle fashion. Such a temperature rise causes an increase in loss of butene-1 due to isomerization and polymerization of butene-1 contained in the starting material mixture, and also causes deterioration of the used catalyst. In order to obviate such serious problems, temperature rise in the reactor must be strictly excluded, for example, by providing a specially designed cooler in the reactor. However, since the thermal conductivity of the ion exchange resin is low, the cooler assembled in the reactor should be of complicated shape, such as multitubular or coiled form. As a result, troublesome operation is necessitated in exchange of the catalyst. Nonetheless, some local portions are raised to high temperature leading to disadvantageous result. On the contrary, in the system operated in the recyclic fashion the temperature throughout the reaction tower may be maintained sufficiently uniformly. However, if the starting mixture is processed through a one-stage recycle system, the polymerization reaction for producing oligomers of isobutylene is suppressed to a lower level as compared to the level attained by a single-pass system, e.g. the piston-flow system, operated at the same temperature. In other words, the proportion of the unreacted isobutylene contained in the reaction mixture relative to the initially contained isobutylene in the starting material is increased. In order to decrease the quantity of unreacted isobutylene, the reaction should be conducted under severer conditions, such that the reaction temperature is raised or the space velosity of the passing liquid is increased. However, when the reaction is conducted under severer conditions, the loss of butene-1 due to isomerization and polymerization is increased, resulting in decrease of remaining butene-1.

According to the advantageous feature of this invention, the starting material mixture is recycled through the first reactor which is operated under the condition at which the formation of oligomers of isobutylene is suppressed below a predetermined level, for instance the conversion rate of isobutylene to oligomers being 70 to 90 wt%, preferably 75 to 85 wt%, and the major portion of unreacted isobutylene, for example not less than 75 wt%, particularly not less than 85 wt%, is reacted in the second reactor. Since the content of isobutylene contained in the mixture fed into the second reactor is reduced considerably, accumulation of reaction temperature causing the temperature difference between the inlet port and the outlet port is not so great. For this reason and additionally for suppressing the isomerization reaction of butene-1 as little as possible, the second reactor is operated by a single-pass system.

In the process of this invention, isomerization of butene-1 can be advantageously suppressed in the case where the butane-butene fraction is saturated with water. In other words, the ratio of unreacted butene-1 relative to unreacted isobutylene in the reaction mixture when the starting material mixture is saturated with water, is higher than that when the starting material mixture is not saturated with water. The content of water for saturating the used butane-butene fraction with water vapor varies within the range of from 50 ppm to 700 ppm depending on the temperature of water contained in the washing vessel in which washing operation is conducted. Although the preferable content of water ranges between 100 ppm and 400 ppm, the content of water is not a critical factor provided that the starting material mixture is saturated with water.

In the process of this invention, the reaction temperature in both of the first and second reactors is 30° to 100° C., preferably 45° to 75° C. If the reaction temperature in either of the reactors is lower than 30° C., the reaction velosity is reduced to too low, resulting in unsatisfactory removal of isobutylene. On the other hand, the reaction temperature in either of the reactors becomes higher than 100° C., participation in reaction of butene-1 is accelerated, resulting in increase of the loss of butene-1.

In the process of this invention, the reaction pressure in both of the first and second reactors is 1 to 50 atm., preferably 5 to 30 atm. If the reaction pressure in the reactor is lower than 1 atm., the reaction in the reaction system is carried out in a vapor phase so that the desired reaction cannot take place satisfactorily. On the other hand, a reaction pressure of higher than 50 atm. is disadvantageous from the industrial standpoint of view, because the reactors and attachment instruments should be pressureproof in order to withstand such a high pressure.

According to this invention, the aforementioned butane-butene fraction is passed through fixed beds each packed with a strongly acidic cation exchange resin to allow isobutylene to polymerize to form oligomers. However, oligomers of isobutylene are absorbed by the cation exchange resin so that the activity of the cation exchange resin is gradually lowered as the system is operated continuously for a long period of time. In order to compensate the reduction in activity of the cation exchange resin, the reaction temperature may be raised to maintain the removal rate of isobutylene by the formation of oligomers thereof at a level higher than a preset rate. However, it has been observed that the content of butene-1 tends to be gradually reduced due to isomerization and polymerization thereof as the reaction temperature is raised. In practice, it is required to maintain the purity of the product butene-1 at a satisfactory high level, for example higher than 99%, and simultaneously to maintain the remaining ratio of butene-1 at a sufficiently high level thereby to maintain the recovery percentage of butene-1 at a high level. In this connection, the remaining ratio as used herein means the proportion of the quantity of butene-1 left in the reaction mixture to the quantity of butene-1 contained in the starting material mixture.

After the initiation of the reaction, the degree of polymerization of isobutylene is gradually lowered with the lapse of time to deteriorate the purity of the product. It is thus required to raise the reaction temperature little by little to maintain the conversion rate of isobutylene at the level of initial stage, for example at a level higher than 90%, particularly higher than 96%. However, as the reaction temperature is raised, the side reactions of butene-1 are accelerated to result in reduction in remaining ratio of butene-1. According to one aspect of this invention, the catalyst may be regenerated when the remaining ratio of butene-1, based on the remaining ratio at the initial stage, after the temperature is raised is lowered to a level of less than 80%, particularly less than 70%.

According to this invention, the cation exchange resin may be regenerated by the steps of stopping passage of the flow of said butane-butene fraction, and then continuously passing a nitrogen gas from the top or bottom of the reaction tower at a temperature of from 20° to 150° C., preferably from 50° to 120° C., and at a space velocity of gas of from 100 to 100,000 1/l.hr, preferably from 1,000 to 30,000 1/l.hr, under a pressure of from 0.1 to 20 atm., preferably 0.5 to 5 atm., over a period of from 5 minutes to 30 hours, preferably from 2 to 10 hours. It is a remarkable fact that the cation exchange resin catalyst can be effectively regenerated by such a simple passage of nitrogen gas. If the nitrogen gas is passed at a temperature of lower than 20° C., the catalyst is not regenerated to have a satisfactory activity. The temperature of higher than 150° C. exceeds the temperature limit allowed by the heat resistivity of the cation exchange resin. Satisfactory regeneration cannot be expected if the space velocity of the nitrogen gas is less than 100 1/l.hr. On the contrary, wasteful consumption of the nitrogen gas is increased with no attendant advantage, if the space velocity of the flowing nitrogen gas is increased more than 100,000 1/l.hr. No more effective operation is realized if the pressure of the flowing nitrogen gas is lower than 0.1 atm, whereas the nitrogen gas pressure of higher than 20 atm. is inconvenient from the operational or economical standpoint of view. Satisfactory regeneration of the cation exchange resin catalyst cannot be expected if the nitrogen gas is flown for a time period of less than 5 minutes, whereas wasteful consumption of the nitrogen gas without any attendant advantage is increased if the nitrogen gas is flown over the period of longer than 30 hours.

The strongly acidic cation exchange resin used in the process of this invention includes cation exchange resins exhibiting strong acidities, and the representative being styrene type sulfonate resins and phenol type sulfonate resins. The styrene type sulfonate cation exchange resins are prepared by sulfonating the resins obtained by co-polymerizing styrene with poly-unsaturated compounds, such as divinylbenzene, and generally represented by the following formula, wherein m and n are positive integers, of:

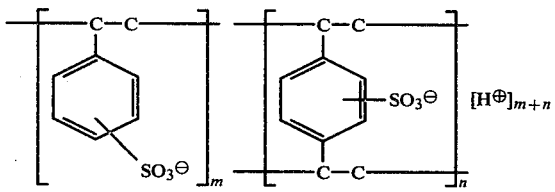

On the other hand, the phenol type sulfonate cation exchange resins are generally prepared by condensing phenolsulfonic acid with formaldehyde, and generally represented by the following formula, wherein m is a positive integer, of:

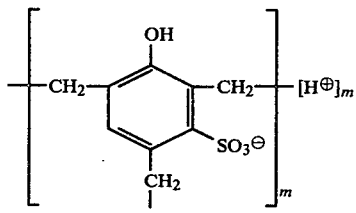

Any of the aforementioned strongly acidic cation exchange resins may be used as the catalyst in the process of this invention, and may be used is the form of spherical or cylindrical particles having an average particle size of from 0.2 to 10 mm.

According to one aspect of the invention, a specific type of storngly acidic cation exchange resin can be used. Where such a specific resin is used, the polymerization reaction of isobutylene is further activated while suppressing the isomerization of butene-1 to butene-2 to a lower level thereby to realize a higher recovery percentage of the product butene-1 of high purity at the subsequent recovery step and the activity of the catalyst is maintained at a higher level for a long period of time. The specific type of strongly acidic cation exchange resin is a styrene type sulfonate cation exchange resin which is prepared by copolymerizing styrene with divinylbenzene followed by sulfonation and which has a surface area of from 0.2 to 120 m$^2$/g, a porosity of from 0.03 to 1.5 ml/ml and an acid exchange capacity of not less than 1.0 meq/g.

Such a cation exchange resin may be prepared, for example, by copolymerizing styrene and divinylbenzene through a suspension polymerization while using a solvent which is a good solvent for the monomers but is poor in swelling the resultant copolymer, such as tertiary amyl alcohol, secondary butanol or isooctane, and then sulfonating the resultant high molecular polymer. The surface area is determined in accordance with the BET Method using the samples dired at 80° C. for 6 hours in vaccuo. The cation exchange resin used in the process of this invention has a surface area of from 0.2 to 120 m$^2$/g, preferably from 2 to 100 m$^2$/g, and more preferably 10 to 80 m$^2$/g. The porosity is determined in accordance with the method described in Prac. Natl. Acad. Sci., Vol 17, page 115 (1921) using mercury, and the cation exchange resin effectively used in the process of this invention has a porosity of from 0.03 to 1.5 ml/ml, preferably 0.05 to 1.2 ml/ml, and more preferably from 0.1 to 1.0 ml/ml. The exchange capacity shows the content of acidic group, and may be determined by titrating HCL generating by the addition of the resin in a 1 N NaCl solution with NaOH. This exchange capacity corresponds to the chamical equivalent (in this invention, the equivalent is shown in milliequivalnet which is 1/1000 of the chemical equivalent) of the sulfonic acid group contained in one gram of the resin. The cation exchange resin used in this invention has an exchange capacity of not less than 1.0 meq/g, preferably from 2.0 to 6.0 meq/g.

It is also preferred that the cation exchange resin used in the process of this invention has a true specific gravity of from 1.0 to 1.4 The resin having all of the aforementioned properties is a resin of macro-network structure and is clearly distinguished from the gel-type cation exchange resins. Meanwhile, the catalytic activity for polymerization of the cation exchange resin may be further improved by blowing the resin with an inert gas at 20° C. to 120° C. to dry the resin prior to use.

The catalyst particles are packed in a first and second pressure-proof, cylindrical reactors to form fixed catalyst beds. The dimensions of both of the catalyst beds contained in the first and second reactors are not critical. The normal height of each bed may range from 0.2 to 20 meters.

The butane-butene fraction containing isobutylene and butene-1 is continuously supplied from either of the top or bottom of each fixed bed, preferably from the top of the bed. The feed rate of the starting material mixture should be such that the space velocity of liquid range from 0.1 to 50

$$\left( \frac{kg}{kg} \times \frac{1}{hr} = \frac{1}{hr} \right),$$

preferably 0.5 to 15 hr.$^{-1}$. The space velocity of liquid as used throughout the specification and claims means the weight (in kg unit) of the flow supplied into the reactor per 1 kg of the catalyst per an hour while excluding the weight of the recirculated flow for the first reactor, and the same term means the weight (in kg unit) of the flow passing through the reactor per 1 kg of the catalyst per an hour for the second reactor. If the space velocity of the supplied butane-butene fraction is less than 0.1 hr$^{-1}$, the yield of the butane-butene fraction after being deprived of isobutylene is lowered to diminish the industrial value of the process. On the contrary, if the space velocity of the supplied material is more than 50 hr$^{-1}$, isobutylene is not removed sufficiently.

According to this invention, about 70 to 90 wt% of isobutylene contained in the starting butane-butene fraction is converted into oligomers in the first reactor, and almost all of the residual isobutylene left unreacted in the first reactor is converted into oligomers in the second reactor so that substantially all of isobutylene contained in the starting material mixture is dimerized or polymerized to form oligomers.

The reaction mixture obtained through the aforementioned reaction is then passed to a distillation tower, and a heavy hydrocarbon fraction mainly composed of dimer and oligomers of isobutylene is discharged from the bottom of the tower and a light hydrocarbon fraction containing butane and butene is discharged from the top of the tower. The distillation is operated through an ordinary process and the number of plates of the distillation tower may be about 3 to 30, for example in the range of 10 to 20.

The light hydrocarbon fraction discharged from the aforementioned distillation tower is then subjected to rectification. This rectification is normally conducted through two stages. By the first stage rectification, isobutane is separated and removed from the top of the distillation tower. The bottom flow from the first rectification or distillation tower is subjected to a further rectification so that the fraction mainly composed of n-butane and butene-2 is removed from the bottom and the product butene-1 is recovered from the top of the tower. For the rectification, two distillation towers having generally 30 to 150 plates, particularly 90 to 140 plates, are used. The thus obtained product butene-1 may be dehydrated using a drying agent, as desired.

In accordance with the process of this invention, the purity of the product butene-1 can be raised to higher than 99%, or further improved to higher than 99.5%. The aforementioned reaction condition may be changed to a more moderate condition or the condition for each of the distillation operations may be changed to a more moderate condition when the required purity of the product is not so high.

According to the process of this invention, the yield of butene-1 recovered by the process is so good that the recovery rate (or remaining ratio thereof in the product) of butene-1 based on the quantity of butene-1 contained in the starting material mixture is higher than 80% or 85% or even higher.

An embodiment of the process according to this invention will now be described by referring to the flow diagram shown in the appended drawing.

Referring to the drawing, feed butane-butene fraction, which may be washed with water prior to introduction if it is desired to saturate the same with water, is introduced through conduits 1 and 2 to a heater $E_1$ where it is heated to a desired temperature, and then passed into a first reactor $R_1$ having a fixed bed packed with particles of a strongly acidic cation exchange resin. The output flow discharged from the first reactor $R_1$ is divided into two flows, and one of these two flows is cooled by a cooler $E_2$ and then recirculated by a recirculation pump P through a conduit 3 to join the fresh butane-butene fraction supplied through the conduit 1 to be fed into the reactor $R_1$. The other of the divided flows is passed through the conduit 4 to a heat exchanger $E_3$ where it is cooled to a desired temperature, and then introduced into a second reactor $R_2$ having a fixed bed packed with particles of a strongly acidic cation exchange resin. The pressure in the reactors $R_1$ and $R_2$ and in the related conduits and apparatuses is controlled at a desired or preset pressure by a pressure control valve PCV. The flow discharged from the reactor $R_2$ is introduced into the valve PCV where the pressure of the flow is reduced, and then the temperature of the flow is controlled by another heat exchanger $E_4$, if necessary. This flow is introduced into a distillation tower $D_1$. Oligomers of isobutylene are removed from the bottom of the tower $D_1$ and discharged through a conduit 6, and the butane-butene fraction deprived of oligomers of isobutylene is distilled from the top of the tower $D_1$ and introduced through a conduit 7 into another distillation tower $D_2$ for rectification. The fraction mainly composed of isobutane is removed from the top of the tower $D_2$, and the bottom fraction from the tower $D_2$ is introduced through a conduit 9 into a further distillation tower $D_3$ for rectification. Butene-1 of high purity is discharged from the top of the tower $D_3$ and recovered through a conduit 10, and the other residual $C_4$-hydrocarbons are discharged from the bottom of the tower $D_3$ and removed through a conduit 11.

The features of this invention will be described in detail with reference to some examples thereof. Incidentally, % indicates % by weight unless otherwise specified.

EXAMPLE 1

Using a reaction system as shown in the drawing, 50 kg of a styrene type sulfonate cation exchange resin (Content of divinylbenzene: about 20%, Acid Exchange Capacity: 4.7 meq/g, Average Particle Size: 0.5 mm $\phi$) was filled in the first reactor $R_1$, and 29.2 kg of the same cation exchange resin was filled in the second reactor $R_2$. A butane-butene fraction containing 3.5% of isobutylene, 30.1% of butene-1, 25.8% of butene-2, 9.5 wt% of isobutane and 31.1% of n-butane was introduced through the conduit 1 into the system at a flow rate of 350 kg/hr. The space velocity of the material liquid was 7.0 hr$^{-1}$. The pressure in the reaction system was maintained at 18 kg/cm$^2$.G by operating the valve PCV. The material flow is joined together with the flow recirculated through the recirculation conduit 3, and introduced through the conduit 2 into the reactor $R_1$. The temperature at the inlet port of the reactor $R_1$ was controlled to 50° C. by the heat exchanger $E_1$. The outlet flow from the reactor $R_1$ was divided into two flows. The recycle ratio was controlled at 10 by the recirculation pump P so that the flow rate of one of the thus divided flows is ten times as large as that of the flow rate of the introduced fresh material. The recycle flow was flown thorugh the conduit 3 and then joined together with the fresh material flow. The other of the divided flow was passed through the conduit 4 and then introduced into the second reactor $R_2$. The remaining ratio of isobutylene in the flow fed into the second reactor $R_2$ was 20.2%, and the remaining ratio of butene-1 in the same flow was 90.0%. In this connection, the remaining ratio means the proportion of the quantity of isobutylene or butene-1 left unreacted in the flow relative to the quantity of isobutylene or butene-1 initially contained in the starting material mixture. The temperature at the inlet port of the reactor $R_2$ was controlled at 50° C. by the heat exchanger $E_3$. The space velocity of the liquid passing through the reactor $R_2$ was 12 hr$^{-1}$. The remaining ratio of isobutylene in the flow discharged from the reactor $R_2$ was 2.8%, and the remaining ratio of butene-1 was 85.5%. The flow was passed through the conduit 5 into the valve PCV where the pressure of the flow was reduced, and then introduced into the distillation tower $D_1$. A butane-butene fraction containing 0.098% of isobutylene and 25.7% of butene-1 was distilled from the top of the tower $D_1$, and oligomers of isobutylene were removed from the bottom of the tower $D_1$. The fraction discharged from the top of the distillation tower $D_1$ was rectified through rectification towers $D_2$ and $D_3$ having theoretical number of plates of 100, and the product butene-1 of a purity of 99.6% was discharged from the top of the tower $D_3$ and recovered through the conduit 10 at a flow rate of 90 kg/hr.

EXAMPLE 2

30 kg of a styrene type sulfonate cation exchange resin (styrene-divinyl benzene copolymer substrate) having a surface area of 48 m²/g, a porosity of 0.3 ml/ml and an acid exchange capacity of 4.9 meq/g (each on dry basis) was charged into each of the reactors $R_1$ and $R_2$. The butane-butene fracton having the same composition as supplied in Example 1 was fed through the conduit 1 into the system at a flow rate of 300 kg/hr, the flow rate corresponding to a space velocity of liquid of 10.0. The temperature at the inlet port of the reactor $R_1$ was 55° C., the recycle ratio was set to 5, and the temperature at the inlte port of the reactor $R_2$ was controlled at 50° C. The other conditions were similar to Example 1. The remaining ratio of isobutylene in the flow passing through the conduit 4 was 25%, and the remaining ratio of butene-1 in the flow passing through the conduit 4 was 93%. The remaining ratio of isobutylene in the flow passing through the conduit 5 was 2.4%, and the remaining ratio of butene-1 in the flow pasisng through the conduit 5 was 87.5%. The flow was introduced thorugh the conduit 5 into the distillation tower $D_1$. A butane-butene fraction containing 0.08% of isobutylene and 25.9% of butene-1 was distilled off from the top of the tower $D_1$, and oligomers of isobutylene were removed from the bottom of the tower $D_1$. A product butene-1 of a purity of 99.7% was discharged from the top of the rectification tower $D_3$ and recovered through the conduit 10 at a flow rate of 79 kg/hr.

EXAMPLE 3

50 kg of the same catalyst as used in Example 1 was charged into the reactor $R_1$, and 20 kg of the same catalyst was charged into the reactor $R_2$. Through the conduit 1 supplied was a butane-butene fraction composed of unreacted $C_4$-hydrocarbon fractions which had been obtained by the steps of removing butadiene from the $C_4$-hydrocarbons prepared by cracking petroleum, subjecting to polymerization in the presence of an aluminum chloride catalyst to form a liquid polymer mixture, and removing the thus formed liquid polymer mixture. The butane-butene fraction contained 5.4% of isobutylene, 37.0% of butene-1, 31.0% of butene-2, 5.9% of isobutane and 20.3% of n-butane, and the fraction was introduced into the system at a flow rate of 200 kg/hr, the flow rate corresponding to a space velocity of liquid passing through the reactor $R_1$ of 4 hr$^{-1}$ and to a space velocity of liquid passing through the reactor $R_2$ of 10 hr$^{-1}$. The temperature at the inlet port of the reactor $R_1$ was controlled at 47° C., the recycle ratio was 10, and the temperature at the inlet port of the reactor $R_2$ was controlled at 50° C. The other conditions were similar to Example 1. The remaining ratio of isobutylene in the flow passing through the conduit 4 was 14.8%, and the remaining ratio of butene-1 in the flow passing through the same conduit was 88.5%. The remaining ratio of isobutylnee in the flow passing through the conduit 5 was 1.5%, and the remaining ratio of butene-1 in the flow passing through the same conduit was 82.4%. A butane-butene fraction containing 0.08% of isobutylene and 30.5% of butene-1 was discharged from the top of the distillation tower $D_1$, and oligomers of isobutylene were removed from the bottom of the tower $D_1$. A product butene-1 of a purity of 99.8% was discharged from the top of the rectification tower $D_3$ and recovered through the conduit 10 at a flow rate of 61 kg/hr.

EXAMPLE 4

The operation as described in Example 1 was continued while gradually raising the reaction temperature to maintain the purity of the product butene-1 at 99.6%. After the lapse of 100 days, the remaining ratio of butene-1 was lowered below 80%, whereupon supply of the starting material mixture was stopped. Then, a nitrogen gas was passed through the conduit 2, the reactor $R_1$, the conduit 4 and the reactor $R_2$ at a temperature of 100° C. and at a flow rate of 400 m³/hr for 8 hours. The flow rate corresponded to the space velocity of the nitrogen gas of 5000 l/l.hr. After the completion of passage of the nitrogen gas, introduction of the starting butane-butene fraction was re-started to find that the cation exchange resin was regenerated to have a catalytic activity substantially equivalent to the initial level.

EXAMPLE 5

Using the system as illustrated in the appended drawing, 30 kg and 22.5 kg of the same catalyst as used in Example 1 were charged, respectively, in the first reactor $R_1$ and the second reactor $R_2$. Through the conduit 1 introduced was a fraction of unreated $C_4$-hydrocarbons obtained by the steps of cracking petroleum to prepare $C_4$-hydrocarbon fraction, removing butadiene from the $C_4$-hydrocarbon fraction by extraction, subjecting the fraction deprived of butadiene to polymerization reaction in the presence of an aluminum chloride catalyst to form a liquid polymer mixture, and then separating the liquid polymer mixture to obtain the fraction of unreacted $C_4$-hydrocarbons. The aforementioned fraction was used as a butane-butene fraction which contained 6.0% of isobutylene, 35.3% of butene-1, 32.5% of butene-2, 5.9% of isobutane and 20.3% of n-butane. The butane-butene fraction was introduced into the system at a flow rate of 180 kg/hr. The sapce velocity of liquid passing through the reactor $R_1$ was 6 hr$^{-1}$, and the space velocity of the liquid passing through the reactor $R_2$ was 8 hr$^{-1}$. The temperature at the inlet port of the reactor $R_1$ was 47° C., the recycle ratio was 10, and the temperature at the inlet port of the reactor $R_2$ was 50° C. The other reaction conditions were similar to Example 1. The remaining ratio of isobutylene in the flow passing through the conduit 4 was 18.8%, and the remaining ratio of butene-1 in the same flow was 91.0%. The remaining ratio of isobutylene in the flow passing through the conduit 5 was 1.5%, and the remaining ratio of butene-1 in the same flow was 85.5%. A butane-butene fraction containing 0.09% of isobutylene and 30.2% of butene-1 was distilled from the top of the distillation tower $D_1$, and oligomers of isobutylene were removed from the bottom of the tower $D_1$. A product butene-1 of a purity of 99.7% was discharged from the top of the rectification tower $D_3$ and recovered through the conduit 10 at a flow rate of 54 kg/hr. The operation was continued while raising the reaction temperature to maintain the purity of the product butene-1 higher than 99.7%. After operating continuously for 70 days, the remaining ratio of butene-1 was reduced below 80%. Whereupon the catalyst in the reactor $R_1$ was regenerated generally in accordance with the procedure described in Example 4 except in that the temperature of the nitrogen gas was 110° C. and the nitrogen gas was flown at a flow rate of 250 m³/hr (corresponding to a space velocity of gas 5000 1/l.hr) for 12 hours. After the completion of passage of the nitrogen gas, the starting butane-butene fraction was introduced again to find that the catalyst was regenerated to have a catalytic activity substantially equivalent to the initial level.

EXAMPLE 6

Using the system as shown in the appended drawing, 50 kg and 30 kg of the same styrene type sulfonate cation exchange resin catalyst as used in Example 1 were charged, respectively, in the reactors $R_1$ and $R_2$. Through the conduit 1 intorduced was a butane-butene fraction containing 350 ppm of water and containing 3.5% of isobutylene, 30.1% of butene-1, 25.8% of butene-2, 9.5% of isobutane and 31.1% of n-butane at a flow rate of 300 kg/hr. The space velocity of liquid passing through the reactor $R_1$ was 6.0 $hr^{-1}$. The pressure in the reaction system was maintained at 18 kg/cm².G by operating the valve PCV. The starting material was jointed together with the flow flowing through the recirculation pass 3, and introduced through the conduit 2 into the reactor $R_1$. The temperature at the inlet port of the reactor $R_1$ was controlled at 48° C. by the heat exchanger $E_1$. The flow discharged from the reactor $R_1$ was divided into two flows. The flow rate of the first flow was adjusted by the recirculation pump P so that it was ten times as large as the flow rate of the introduced starting material, in other words the recycle ratio was maintained at 10. This recirculated first flow joined together with the fresh feed material. The second flow from the reactor $R_1$ was passed thorugh the conduit 4 into the reactor $R_2$. The remaining ratio of isobutylene in this second flow was 19.8%, and the remaining ratio of butene-1 in the same flow was 91.2%. The tempeatrure at the inlet port of the reactor $R_2$ was controlled at 48° C. by the heat exchanger $E_3$. The space velocity of the liquid passing through the reactor $R_2$ was 1 $hr^{-1}$. The remaining ratio of isobutylene in the flow discharged from the reactor $R_2$ was 2.7%, and the remaining ratio of butene-1 in the same flow was 87.6%. This flow was passed thorugh the conduit 5 into the valve PCV where the pressure thereof was reduced, and then introduced into the distillation tower $D_1$. A butane-butene fraction containing 0.095% of isobutylene and 26.4% of butene-1 was distilled from the top of the distillation tower, and oligomers of isobutylene were removed from the bottom of the tower. The fraction distilled from the top of the distillation tower $D_1$ as subjected to rectification in the distillation towers $D_2$ and $D_3$ having the theoretical number of plates of 100, and a product butene-1 of a purity of 99.7% was separated from the top of the tower $D_3$ and recovered thorugh the conduit 10 at a flow rate of 79 kg/hr. The reaction temperature was raised as the purity of the product butene-1 was lowered. The system was continuously operated while repeating periodically the operation of raising the reaction temperature. After operating the system for 3 months, the remaining ratio of butene-1 became below 80%.

EXAMPLE 7

50 kg and 20 kg of the same catalyst as used in Example 1 were charged in the reactors $R_1$ and $R_2$. Through the conduit 1 introduced was a butane-butene fraction containing 5.4% of isobutylene, 37.0% of butene-1, 31.0% of butene-2, 5.9% of isobutane and 20.3% of n-butane, and being washed with water in a washing vessel. The butane-butene fraction had been obtained by the steps of cracking petroleum to prepare $C_4$-hydrocarbons, removing butadiene from the $C_4$-hydrocarbons by extraction, subjecting to polymerization in the presence of an aluminum chloride catalyst to form a liquid polymer mixture, and then recovering unreacted $C_4$-hydrocarbon fraction. The aforementioned butane-butene fraction was introduced into the system at a flow rate of 250 kg/hr, the flow rate corresponding to the space velocity of the liquid passing through the reactor $R_1$ of 5 $hr^{-1}$ and the space velocity of the liquid passing through the reactor $R_2$ of 12.5 $hr^{-1}$. The temperature at the inlet port of the reactor $R_1$ was 47° C., the recycle ratio was 8, and the temperature at the inlet port of the reactor $R_2$ was 50° C. The other reaction conditions were the same as in Example 6. The remaining ratio of isobutylene in the flow passing through the conduit 4 was 15.9%, and the remaining ratio of butene-1 in the same flow was 90.6%. The remaining ratio of isobutylene in the flow passing through the conduit 5 was 1.9%, and the remaining ratio of butene-1 in the same flow was 85.4%. A butane-butene fraction containing 0.10% of isobutylene and 31.6% of butene-1 was distilled from the top of the distillation tower $D_1$, and oligomers of isobutylene were removed from the bottom of the tower $D_1$. A product butene-1 of a purity of 99.8% was separated from the top of the rectification tower $D_3$ and recovered through the conduit 10 at a flow rate of 79 kg/hr.

What is claimed is:

1. A process for isolating and recovering butene-1 of high purity at a high yield comprising the steps of continuously passing a butane-butene fraction containing 0.1 to 15 wt% of isobutylene and 10 to 50 wt% of butene-1 through a first reactor packed with a strongly acidic cation exchange resin having an average particle size of from 0.2 to 10 mm at a temperature of from 30° to 100° C. and at a space velocity of liquid of from 0.1 to 50 $hr^{-1}$ under a pressure of from 1 to 50 atom., dividing the output mixture flowing out of said first reactor into two flows at a division ratio in flow rate of 1∼15:1, recirculating the first flow having the flow rate of 1∼15 into said first reactor packed with said cation exchage resin, passing the second flow having the flow rate of 1 through a second reactor packed with a strongly acidic cation exchange resin having an average particle size of from 0.2 to 10 mm at a temperature of from 30° to 100° C. and at a space velocity of liquid of from 0.1 to 50 $hr^{-1}$ under a pressure of from 1 to 50 atm., distilling the output flow from said second reactor to separate the same into a heavy hydrocarbon fraction containing oligomers of isobutylene as the main ingredient and a light hydrocarbon fraction containing butane and butene as the main ingredients, and rectifying said light hydrocarbon fraction to isolate butene-1 from other $C_4$-hydrocarbons.

2. A process for isolating and recovering butene-1 according to claim 1, wherein said butane-butene fraction is saturated with water.

3. A process for isolating and recovering butene-1 according to claim 1, wherein said butane-butene fraction containing 0.1 to 15 wt% of isobutylene and 10 to 50 wt% of butene-1 is a mixture of unreacted $C_4$-hydrocarbons obtained at the step of the preparatin of a liquid or semi-solid polymer by polymerizing a mixture of starting C4-hydrocarbons in the presence of an aluminum chloride catalyst, said starting C4-hydrocarbons being those which are obtained by cracking petroleum and from which butadiene is separated and removed.

4. A process for isolating and recovering butene-1 according to claim 1, wherein said butane-butene fraction containing 0.1 to 15 wt% of isobutylene and 10 to 50 wt% of butene-1 is a mixture of unreacted C4-hydrocarbons obtained at the step of the preparation of methyl tert-butyl ether by reacting a mixture of starting C4-hydrocarbons with methanol in the presence of an acidic catalyst, said starting C4-hydrocarbons being those which are obtained by cracking petroleum and from which butadiene is separated and reomoved.

5. A process for isolating and recovering butene-1 according to claim 1, wherein said butane-butene fraction containing 0.1 to 15 wt% of isobutylene and 10 to 50 wt% of butene-1 is a mixture of unreacted C4-hydrocarbons obtained at the step of the preparation of tert-butyl alcohol by reacting a mixture of starting C4-hydrocarbons with water in the presence of an acidic catalyst, said starting C4-hydrocarbons being those which are obtained by cracking petroleum and from which butadiene is separated and removed.

6. A process for isolating and recovering butene-1 according to any of claims 3, 4 or 5, wherein said mixture of unreacted C4-hydrocarbons is washed with water to allow said butane-butene fraction to be saturated with water.

7. A process for isolating and recovering butene-1 according to claim 1, further comprising the steps of stopping the supply of said butane-butene fraction when the rate of remaining butene-1 is substantially lowered, continuously passing gaseous nitrogen through said first and second reactors at a temperature of from 20° to 150° C. and at a space velocity of gas of from 100 to 100,000 hr$^{-1}$ under a pressure of from 0.1 to 20 atm. over a period of from 5 minutes to 30 hours to regenerate the catalytic activity of said cation exchange resin, and then re-starting the supply of said butane-butene fracton to allow the same to pass through said first and second reactors continuously.

8. A process for isolating and recovering butene-1 according to claim 7, wherein regeneration of said cation exchange resin is started when the rate of remaining butene-1 reaches less than 80%.

9. A process for separating and recovering butene-1 according to claim 1, wherein said cation exchange resin is selected from the group consisting of styrene type sulfonate cation exchange resins represented by the following general formula of:

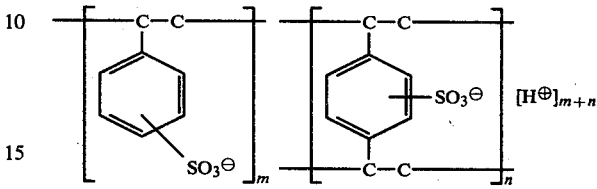

wherein m and n are positive integers, and phenol type sulfonate cation exchange resins represented by the following general formula of:

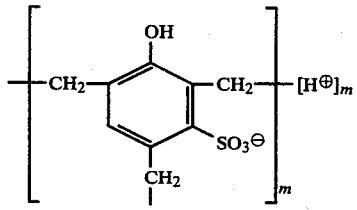

wherein m is a positive integer.

10. A process for isolating and recovering butene-1 according to claim 9, wherein said styrene type sulfonate cation excahnge resins have a surface area of from 0.2 to 120 m$^2$/g, a porosity of from 0.03 to 1.5 ml/ml and an acid exchange capacity of not less than 1.0 meq/g.

11. A process for isolating and recovering butene-1 according to claim 10, wherein said cation exchange resin is dried by blowing the same with an inert gas maintained at a temperature of from 20° C. to 120° C. prior to use.

* * * * *